United States Patent [19]

Billheimer et al.

[11] Patent Number: 4,900,744
[45] Date of Patent: Feb. 13, 1990

[54] ANTIHYPERCHOLESTEROLEMIC 4,5-DIARYL-2-SUBSTITUTED THIOIMIDAZOLES

[75] Inventors: Jeffrey T. Billheimer, West Chester, Pa.; Peter J. Gillies, Hockessin; Wendell W. Wilkerson, New Castle, both of Del.

[73] Assignee: E. I. Du Pont de Nemours and Company, Wilmington, Del.

[21] Appl. No.: 244,170

[22] Filed: Sep. 14, 1988

[51] Int. Cl.⁴ .................. A61K 31/415; C07D 233/84
[52] U.S. Cl. ..................................... 514/398; 548/337
[58] Field of Search .......................... 548/337; 514/398

[56] References Cited

U.S. PATENT DOCUMENTS 4,355,039 10/1982 Niedballa et al. .................... 514/398
4,654,358 3/1987 Lautenschläger et al. ..... 548/337 X
4,734,421 3/1988 Hammond et al. ............. 548/337 X Primary Examiner—Richard A. Schwartz

[57] ABSTRACT

Antihypercholesterolemic thioimidazoles of the formula

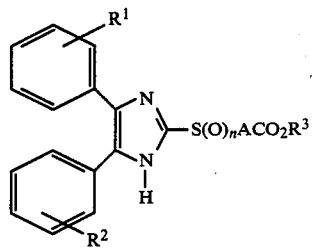

or a pharmaceutically acceptable salt thereof, wherein
$R^1$ and $R^2$ independently are H, F, Cl, $CF_3$, alkyl of 1 to 4 carbon atoms, or alkoxy of 1 to 4 carbon atoms;
A is alkylene of 7–20 carbon atoms or an alkenyl residue thereof with no more than 2 double bonds;
$R^3$ is H, $CH_3$ or $C_2H_5$; and
n is 0, 1 or 2, are provided, such as 8-(4,5-diphenyl-1H-imidazol-2-ylthio)octanoic acid ethyl ester.

24 Claims, No Drawings

ANTIHYPERCHOLESTEROLEMIC 4,5-DIARYL-2-SUBSTITUTED THIOIMIDAZOLES

BACKGROUND OF THE INVENTION

This invention relates to 4,5-diaryl-2-substituted thioimidazoles as inhibitors of acyl-CoA:cholesterol acyltransferase (ACAT), processes for their preparation, and use as antihypercholesterolemic agents.

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells is esterified by ACAT prior to its incorporation and secretion into the bloodstream as chylomicrons, inhibition of ACAT can reduce the absorption of dietary cholesterol.

Lautenschlgäger et al. in U.S. Pat. No. 4,654,358 disclose imidazol-2-yl mercapto alkanoic acids having the formula

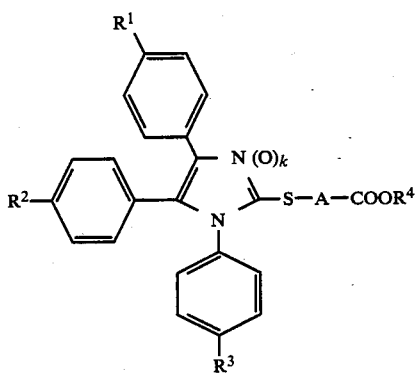

and a process for the treatment of humans suffering from inflammatory diseases or diseases in relation with the lipid metabolism wherein
k is the numeral 0, 1 or 2,
$R^1$, $R^2$ and $R^3$ which are the same or different from each other, are a member selected from the group consisting of hydrogen, fluorine, chlorine, methyl, methoxy and trifluoromethyl,
$R^4$ is a member selected from the group consisting of hydrogen, sodium, potassium, methyl, ethyl, propyl, isopropyl and butyl, and
A is a member selected from the group consisting of the groups

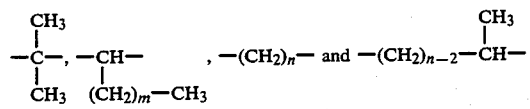

wherein m is zero or a numeral from 1 to 8 and n is a numeral from 2 to 10.

Niedballa et al. in U.S. Pat. No. 4,355,039 describe imidazole derivatives of the formula

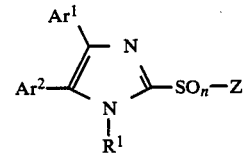

wherein
$Ar^1$ and $Ar^2$ are each phenyl; phenyl substituted by halogen, $C_{1-4}$ alkyl, $C_{1-4}$ alkoxy or $C_{2-6}$ dialkylamino; pyridyl; furyl; or thienyl; with the proviso that $Ar_1$ and $Ar_2$ are not both unsubstituted phenyl;
$R^1$ is hydrogen, $C_{1-4}$ alkly or $C_{1-4}$ alkyl substituted by hydroxy, $C_{1-4}$ alkoxy or $C_{1-6}$ alkanoyloxy;
n is 0, 1 or 2; and
Z is a $C_{2-6}$-alkyl or -alkenyl residue substituted by one or two of hydroxy, $C_{1-4}$ alkoxy, $C_{2-8}$ alkylenedioxy, $C_{1-6}$ alkanoyloxy or benzolyloxy, or by one alkoxycarbonyl group;
and the salts thereof with physiologically acceptable acids, possess valuable pharmacological properties, e.g., anti-inflammatory activity.

Niedballa et al. in U.S. Pat. No. 4,402,960 describe imidazole derivatives of the formula

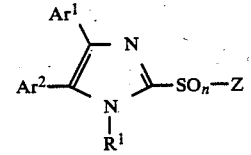

wherein
$Ar^1$ and $Ar^2$ each independently is phenyl, optionally substituted by halogen atoms, alkyl residues, alkoxy residues; or dialkylamino residues; pyridyl, furyl; or thienyl;
$R^1$ is hydrogen; alkyl of 1–6 carbon atoms optionally substituted by hydroxy groups, alkoxy groups, or acyloxy groups; benzyl; tetrahydropyran-2-yl; or tetrahydrofuran-2-yl;
n is 0, 1 or 2 ; and
Z is phenyl optionally substituted by halogen atoms, alkyl groups, alkoxy groups, nitro groups, amino, acylamino groups or trifluoromethyl groups; pyridyl; N-oxypyridyl; pyrimidinyl; thiazolyl; or thienyl, and the physiologically acceptable salts thereof with acids, have valuable pharmacological activity, e.g., anti-inflammatory activity.

Lautenschlager et al. in U.S. Pat. No. 4,460,598 describe new triphenylimidazolyloxyalkanoic acids of the general formula

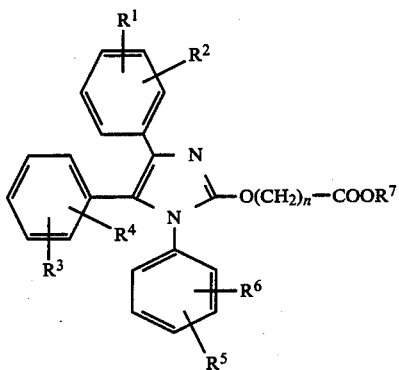

and a process for the treatment of thromboembolic inflammatory and/or atherosclerotic diseases in humans by using the same wherein n denotes an integer from 1 to 10, while $R^1$, $R^2$, $R^3$, $R^4$, $R^5$ and $R^6$ which are identical or different from each other, are members selected from the group consisting of hydrogen, the halogens, alkyl, preferably $C_{1-4}$-alkoxy, and trifluoromethyl, and one or several of the groupments $R^1$ and $R^2$, $R^3$ and $R^4$, and $R^5$ and $R^6$ together, a methylenedioxy group. Particularly suitable and, therefor, preferred are hydrogen, methyl, ethyl, n- and isopropyl, fluorine, chlorine, bromine, methoxy and ethoxy, hydrogen being most preferred. $R^7$ is a member selected from the group consisting of hydrogen, the alkali metal ions, the straight-chain or branched alkyl group with 1 to 6 carbon atoms, such as, for example, methyl, ethyl, propyl, isopropyl, butyl or isobutyl, and the benzyl group. The methyl and the ethyl groups being the preferred alkyl groups.

Ferrini et al. in U.S. Pat. No. 4,308,277 describe compounds of the formula

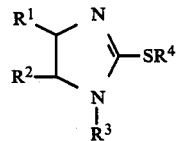

in which $R^1$ and $R^2$ independently of one another are substituted or unsubstituted aryl or hetero-aryl groups, $R^3$ is hydrogen or lower alkyl and $R^4$ is a substituted or unsubstituted aliphatic hydrocarbon radical (i.e., of lower carbon atom content), and their pharmaceutically usable salts. These compounds possess immunoregulatory, antithrombotic and antiinflammatory properties and can be used as active ingredients in medicaments.

Niedballa et al. in U.S. Pat. No. 4,272,543 describe imidazole derivatives of the formula

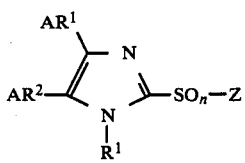

wherein $AR^1$ and $AR^2$ are independently each phenyl; phenyl substituted by halogen, $C_{1-4}$ alkyl, $C_{1-4}$ alkoxy or $C_{2-6}$ dialkylamino; pyridyl; furyl; or thienyl; with the proviso that $AR_1$ and $AR_2$ are not both unsubstituted phenyl;

$R^1$ is hydrogen, alkyl of 1-4 carbon atoms or alkyl of 1-4 carbon atoms substituted by hydroxy, $C_{1-4}$ alkoxy or $C_{1-6}$ alkanoyloxy;

n is 0, 1 or 2; and

Z is cyano; alkynyl of 2-6 carbon atoms; cycloalkyl of 3-8 carbon atoms; cycloalkyl of 3-8 carbon atoms substituted by hydroxy, acyloxy, hydroxymethyl or acyloxymethyl, "acyl" in both cases being the acyl group of a hydrocarbon, aliphatic $C_{1-6}$ carboxylic acid or of benzoic acid; or alkyl or 1-4 carbon atoms substituted by cyano, phenyl or cycloalkyl of 3-6 carbon atoms;

or physiologically acceptable salts thereof with an acid, have valuable pharmacological properties (antiinflammatory, antiallergic and immunostimulating activity).

Cherkofsky et al. in U.S. Pat. No. 4,182,769 describe compounds of the formula

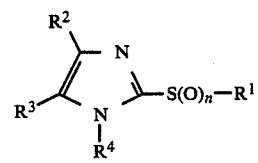

where n=0, 1, or 2;

$R^1$ = $C_1$-$C_6$ alkyl; allyl; vinyl; —$CH_2COCH_3$; —$CH_2$-$S(O)_m$, $CH_3$, where m=0, 1 or 2; mono- and polyhalo $C_1$-$C_4$ alkyl;

$R^2$ and $R^3$, the same or different =

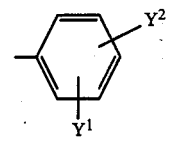

$Y^1$ and $Y^2$, the same or different=hydrogen, $C_1$-$C_4$ alkoxy, $C_1$-$C_4$ alkyl, Cl, F, $CF_3$, $NH_2$, —$N(CH_3)_2$, $NO_2$, $CH_3S$—, $CH_3SO_2$—, or $Y_1$ and $Y_2$ taken together forming a dioxymethylene brige; provided when $R^1$=$C_1$-$C_4$ alkyl, $C_3$-$C_4$ haloalkyl with halogen substituted at the 3 or 4 position, allyl, or acetonyl, both $Y^1$ and $Y^2$ cannot be H;

$R^4$=$C_1$-$C_6$ alkyl, allyl, $CH_2CH_2N(R^5)_2$,

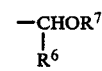

2-tetrahydropyranyl, 2-tetrahydrofuranyl, and many additional groups other than H. These compounds are useful for treating arthritis and related diseases.

Doebel et al. in U.S. Pat. No. 3,636,003 describe certain derivatives of 2-mercaptoimidazole which have anti-inflammatory utility. These compounds have the formula

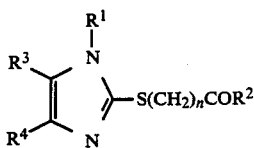

wherein $R^1$ is lower alkyl, phenyl substituted by lower alkyl, lower alkoxy, halogen or trifluoromethyl;

$R^2$ is hydroxy or lower alkoxy;

$R^3$ is hydrogen or lower alkyl;

$R^4$ is lower alkyl, phenyl or phenyl substituted; lower alkyl, lower alkoxy, halogen or trifluoromethyl; and n is 0 or 1.

Doebel et al. in U.S. Pat. No. 3,488,423 describe a process for producing antiinflammatory effects in warm-blooded animals by administering to them certain derivatives of 2-mercaptoimidazole in effective amounts. The compounds useful in the claimed process can be represented by the following structural formula:

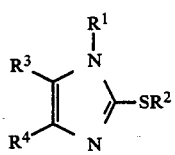

wherein $R^1$ is lower alkyl; lower alkenyl; cycloalkyl; cycloalkyl-lower-alkyl; monocarbocyclic aryl; mono-carbocyclic aryl-lower-alkyl; di-lower-alkylamino-lower-alkyl; lower alkoxy-lower-alkyl; or pyridyl;

$R^2$ represents hydrogen, di-lower-alkylamino-lower-alkyl, carbo(lower)alkoxy or lower alkylcarboxy;

$R^3$ stands for hydrogen or lower alkyl, and $R^4$ denotes hydrogen, lower alkyl or monocarbocyclic aryl.

SUMMARY OF THE INVENTION

According to the present invention there are provided compounds of the formula:

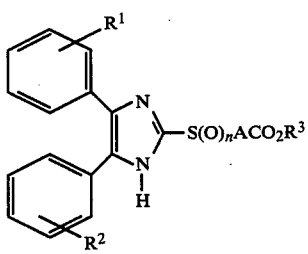

or a pharmaceutically acceptable salt thereof, wherein $R^1$ and $R^2$ independently are H, F, Cl $CF_3$, alkyl of 1 to 4 carbon atoms, or alkoxy of 1 to 4 carbon atoms;

A is alkylene of 7–20 carbon atoms or an alkenyl residue thereof with no more than 2 double bonds;

$R^3$ is H, $CH_3$ or $C_2H_5$; and n is 0, 1 or 2.

Also provided are pharmaceutical compositions consisting essentially of a suitable pharmaceutical carrier and an ACAT-inhibitory effective amount of a compound of Formula (I) above, and methods of using the compounds of Formula (I) to inhibit intestinal absorption of cholesterol.

Further provided are processes for preparing compounds of Formula (I), which processes will be described in detail hereinafter.

PREFERRED EMBODIMENTS

Preferred compounds are those compounds of Formula (I) wherein:

(a) $R^1$ and $R^2$ are H; and/or (b) A is alkylene of 7 to 10 carbon atoms.

Specifically preferred compounds are:

(a) 8-(4,5-diphenyl-1H-imidazol-2-ylthio)octanoic acid ethyl ester.

(b) 8-(4,5-diphenyl-1H-imidazol-2-ylthio)octanoic acid.

(c) 11-(4,5-diphenyl-1H-imidazol-2-ylthio)undecanoic acid ethyl ester.

(d) 11-(4,5-diphenyl-1H-imidazol-2-ylthio)undecanoic acid.

Synthesis

The 4-imidazolin-2-thione starting materials (2) are available from commercial sources or are produced by literature methods, for example, by condensing a benzoin (1a) with thiourea (1b) in a polar inert solvent such as dimethylformamide as shown in Scheme I. Alternatively, the starting materials (2) are produced by known processes from the corresponding 4-imidazolin-2-ones by reaction with Lawesson's reagent or diphosphorus pentasulfide in an aprotic solvent such as toluene. The esters of Formula I (3) may be prepared by known processes, for example, by alkylation in a polar inert solvent such as dimethylformamide with an alkylating agent of the formula $X-A-CO_2R^3$, where A has the meaning as given in the definition of Formula (I) and $R^3$ is $CH_3$ or $C_2H_5$, and X is a halogen, preferably Br. These esters may be hydrolyzed to the corresponding acids of Formula (I) (4) by known processes, for example, by reaction in aqueous, aqueous-organic, or organic solvents such as water, alcohols, ethers, or mixtures thereof with an alkali metal hydroxide and then acidified with an inorganic mineral acid. The methods described herein are substantially similar to the methods described in U.S. Pat. No. 4,654,358.

The sulfones of Formula (I) (5, n=2) are prepared from their respective esters by known processes of oxidation of sulfides, for example, using Oxone ® (potassium peroxymonosulfate), two equivalents, in inert solvents such as lower alcohols. Sulfoxides of Formula (I) (5, n=1) are prepared via usual procedures such as oxidation of sulfides using one equivalent of a peracid, for example, metachloroperbenzoic acid, in an inert solvent such as methylene chloride (Scheme II).

Scheme I
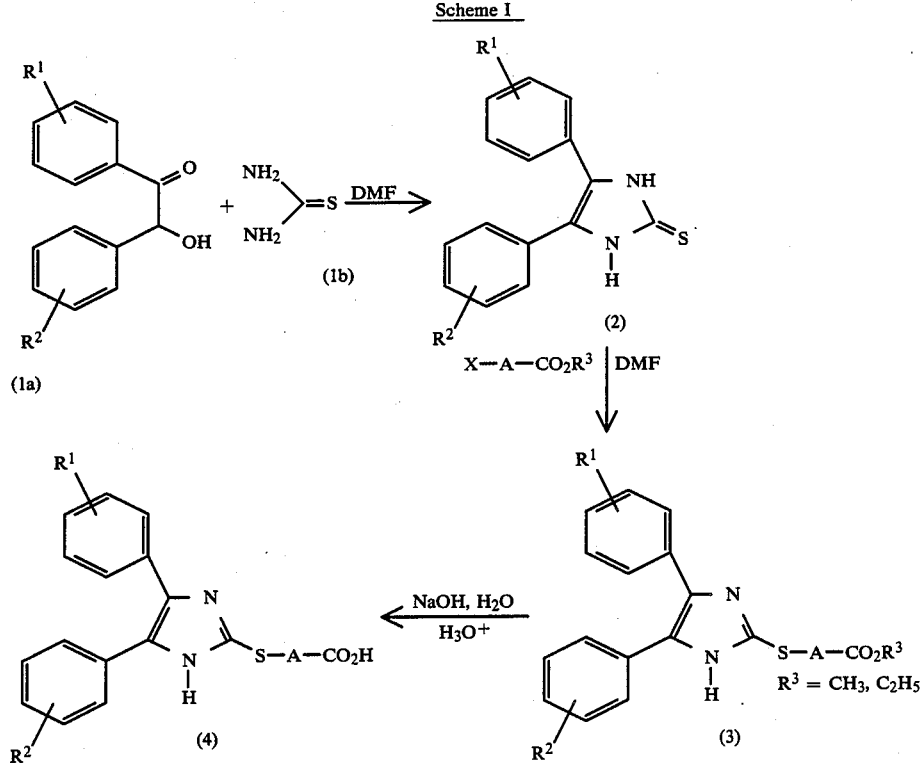
Scheme II
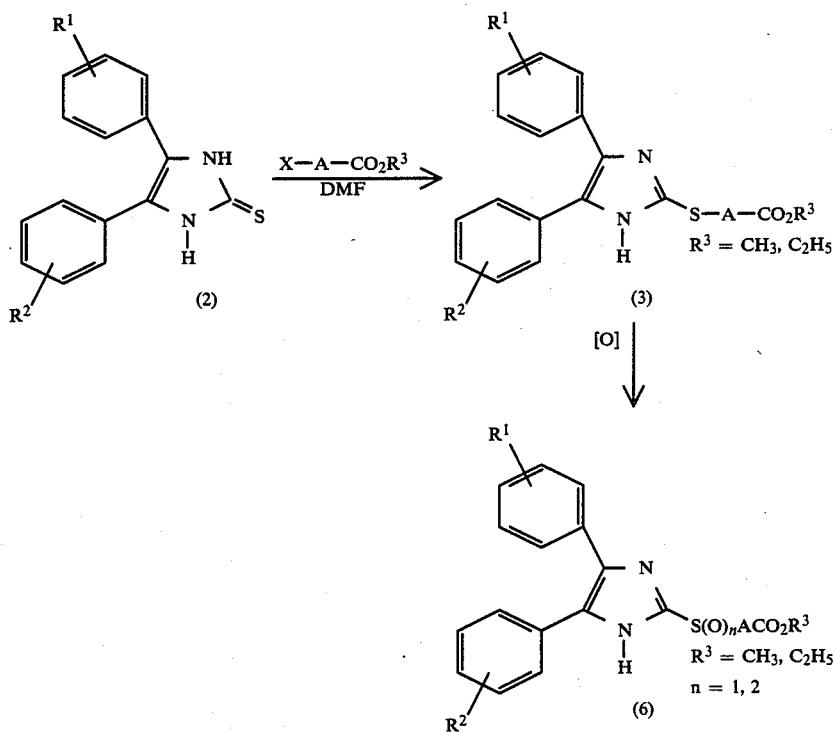
The invention can be further understood by reference to the following examples in which parts and percentages are by weight.

8-(4,5-Diphenyl-1H-imidazol-2-ylthio)octanoic acid ethyl ester

To a solution of 7.57 g (0.03 mole) 4,5-diphenyl-2-imidazolethiol in 75 ml dimethylformamide was added, dropwise, 7.23 g (0.03 mole) ethyl-8-bromooctanoate in 25 ml dimethylformamide. The reaction mixture was stirred at reflux under nitrogen overnight. The cooled solution was poured into 5% sodium bicarbonate and ice and then extracted with ethyl acetate. The organic layer was backwashed with 5% sodium bicarbonate, water, and saturated sodium chloride solution, then dried over magnesium sulfate and the solvent was removed under vacuum. The residue was chromatographed using hexane:ethyl acetate (7:3). The resulting solid was recrystallized from ethanol and triturated with hexane to give 9.12 g (0.022 mole) of the title compound as a white solid, mp=77°-79° C. H$^1$NMR(DMSO-d6): δ12.6(s,1H), 7.7-7.1(m,10H), 4.0(q,2H,J=8Hz), 3.1(t,2H,J=7Hz), 2.3(t,2H,J=17Hz), 1.8-1.1(m,13H).

EXAMPLE 2

11-(4,5-Diphenyl-1H-imidazol-2-ylthio)undecanoic acid ethyl ester

To a solution of 12.6 g (0.05 mole) 4,5-diphenyl-2-imidazolethiol in 125 ml dimethylformamide was added, dropwise, 14.2 g (0.05 mole) ethyl-11-bromoundecanoate in 40 ml dimethylformamide and the reaction mixture was stirred at reflux under nitrogen overnight. The cooled solution was poured into 5% sodium bicarbonate and ice and then extracted with ethyl acetate. The organic layer was backwashed with 5% sodium bicarbonate, water, and saturated sodium chloride solution, then dried over magnesium sulfate and the solvent was removed under vacuum. The residue was chromatographed using hexane:ethyl acetate (9:1). The resulting solid was triturated with hexane to give 13.58 g (0.029 mole) of the title compound as a white solid, mp=57°-59° C. $^1$HNMR(DMSO-d6): δ12.6(s,1H), 7.6-7.1(m,10H), 4.0(q,2H,J=8Hz), 3.5(t,2H,J=7Hz), 2.25(t,2H,J=7Hz), 1.8-1.1(m.21H).

EXAMPLE 3

8-(4,5-Diphenyl-1H-imidazol-2-yl)sulfonyl)octanoic acid ethyl ester

To a solution of 1.50 g (0.0036 mole) 8-(4,5-diphenyl-1H-imidazol-2-ylthio)octanoic acid ethyl ester in 50 ml methanol was added, portionwise as a solid, 4.43 g (0.0072 mole) Oxone®. The reaction mixture was stirred at room temperature under nitrogen for 7 hours. The solid was filtered and washed with methanol. The filtrate was concentrated and then partitioned between ethyl acetate and water. The organic layer was dried over magnesium sulfate and the solvent removed under vacuum. The resulting solid was triturated with hexane to give 1.35 g of the title compound as white solid, mp=95°-96° C. $^1$HNMR(CDCl$_3$): δ 11.0(s,1H), 7.7-7.1(m,10H), 4.1(q,2H,J=8Hz), 3.4(t,2H,J=7Hz), 2.3(t,2H,J=7Hz), 1.9-1.1(m,13H).

The compounds of Examples 1-3 are listed in Table 1 along with other compounds which were or can be prepared by the methods described in Examples 1-3.

TABLE 1

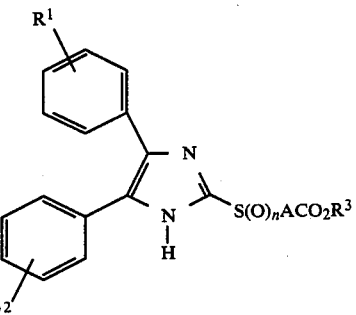

| No. | R$^1$ | R$^2$ | R$^3$ | n | A | mp (°C.) |
|---|---|---|---|---|---|---|
| 1 | H | H | C$_2$H$_5$ | 0 | (CH$_2$)$_7$ | 77–79 |
| 2 | H | H | C$_2$H$_5$ | 0 | (CH$_2$)$_{10}$ | 57–59 |
| 3 | H | H | C$_2$H$_5$ | 2 | (CH$_2$)$_7$ | 95–96 |
| 4 | H | H | C$_2$H$_5$ | 1 | (CH$_2$)$_7$ | |
| 5 | H | H | CH$_3$ | 0 | (CH$_2$)$_7$ | |
| 6 | H | H | CH$_3$ | 2 | (CH$_2$)$_7$ | |
| 7 | 4-F | 4-F | CH$_3$ | 0 | (CH$_2$)$_7$ | |
| 8 | 4-Cl | 4-Cl | CH$_3$ | 0 | (CH$_2$)$_7$ | |
| 9 | 4-CF$_3$ | 4-CF$_3$ | CH$_3$ | 0 | (CH$_2$)$_7$ | |
| 10 | 4-CH$_3$ | 4-CH$_3$ | CH$_3$ | 0 | (CH$_2$)$_7$ | |
| 11 | 4-F | 4-Br | C$_2$H$_5$ | 0 | (CH$_2$)$_7$ | |
| 12 | 4-Cl | H | C$_2$H$_5$ | 0 | (CH$_2$)$_7$ | |
| 13 | 4-CF$_3$ | H | C$_2$H$_5$ | 0 | (CH$_2$)$_7$ | |
| 14 | 4-F | 4-F | C$_2$H$_5$ | 0 | (CH$_2$)$_7$ | |
| 15 | 4-Cl | 4-Cl | C$_2$H$_5$ | 0 | (CH$_2$)$_7$ | |
| 16 | 4-CF$_3$ | 4-CF$_3$ | C$_2$H$_5$ | 0 | (CH$_2$)$_7$ | |
| 17 | 4-CH$_3$ | 4-CH$_3$ | C$_2$H$_5$ | 0 | (CH$_2$)$_7$ | |
| 18 | 4-C$_2$H$_5$ | 4-C$_2$H$_5$ | C$_2$H$_5$ | 0 | (CH$_2$)$_7$ | |
| 19 | 4-C$_3$H$_7$ | 4-C$_3$H$_7$ | C$_2$H$_5$ | 0 | (CH$_2$)$_7$ | |
| 20 | 4-C$_4$H$_9$ | 4-C$_4$H$_9$ | C$_2$H$_5$ | 0 | (CH$_2$)$_7$ | |
| 21 | 4-OCH$_3$ | 4-OCH$_3$ | CH$_3$ | 0 | (CH$_2$)$_7$ | |
| 22 | 4-OC$_2$H$_5$ | H | C$_2$H$_5$ | 0 | (CH$_2$)$_7$ | |
| 23 | 4-OC$_3$H$_7$ | H | C$_2$H$_5$ | 0 | (CH$_2$)$_7$ | |
| 24 | 4-OC$_4$H$_9$ | 4-OC$_4$H$_9$ | CH$_3$ | 0 | (CH$_2$)$_7$ | |
| 25 | 4-OCH$_3$ | 4-OCH$_3$ | C$_2$H$_5$ | 0 | (CH$_2$)$_7$ | |
| 26 | 4-OC$_2$H$_5$ | 4-OC$_2$H$_5$ | C$_2$H$_5$ | 0 | (CH$_2$)$_7$ | |

TABLE 1-continued

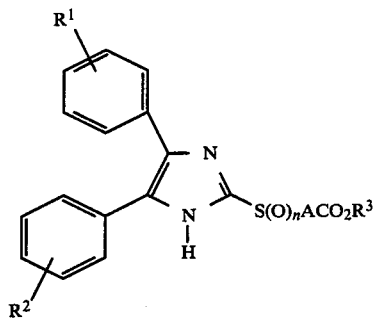

| No. | R¹ | R² | R³ | n | A | mp (°C.) |
|---|---|---|---|---|---|---|
| 27 | 4-OC$_3$H$_7$ | 4-OC$_3$H$_7$ | C$_2$H$_5$ | 0 | (CH$_2$)$_7$ | |
| 28 | 4-OC$_4$H$_9$ | 4-OC$_4$H$_9$ | C$_2$H$_5$ | 0 | (CH$_2$)$_7$ | |
| 29 | H | H | C$_2$H$_5$ | 0 | (CH$_2$)$_8$ | |
| 30 | H | H | C$_2$H$_5$ | 0 | (CH$_2$)$_9$ | |
| 31 | H | H | C$_2$H$_5$ | 0 | (CH$_2$)$_{10}$ | |
| 32 | H | H | C$_2$H$_5$ | 0 | (CH$_2$)$_{11}$ | |
| 33 | H | H | C$_2$H$_5$ | 0 | (CH$_2$)$_{12}$ | |
| 34 | H | H | C$_2$H$_5$ | 0 | (CH$_2$)$_{13}$ | |
| 35 | H | H | C$_2$H$_5$ | 0 | (CH$_2$)$_{14}$ | |
| 36 | H | H | C$_2$H$_5$ | 0 | (CH$_2$)$_{15}$ | |
| 37 | H | H | C$_2$H$_5$ | 0 | (CH$_2$)$_{16}$ | |
| 38 | H | H | C$_2$H$_5$ | 0 | (CH$_2$)$_{17}$ | |
| 39 | H | H | C$_2$H$_5$ | 0 | (CH$_2$)$_{18}$ | |
| 40 | H | H | C$_2$H$_5$ | 0 | (CH$_2$)$_{19}$ | |
| 41 | H | H | C$_2$H$_5$ | 0 | (CH$_2$)$_{20}$ | |
| 42 | H | H | C$_2$H$_5$ | 0 | CH=CH(CH$_2$)$_5$ | |
| 43 | H | H | C$_2$H$_5$ | 0 | CH$_2$CH=CH(CH$_2$)$_4$ | |
| 44 | H | H | C$_2$H$_5$ | 0 | (CH$_2$)$_2$CH=CH(CH$_2$)$_3$ | |
| 45 | H | H | C$_2$H$_5$ | 0 | (CH$_2$)$_3$CH=CH(CH$_2$)$_2$ | |
| 46 | H | H | C$_2$H$_5$ | 0 | (CH$_2$)$_4$CH=CHCH$_2$ | |
| 47 | H | H | C$_2$H$_5$ | 0 | (CH$_2$)$_5$CH=CH | |
| 48 | H | H | C$_2$H$_5$ | 0 | (CH$_2$)$_8$CH=CH(CH$_2$)$_7$ | |
| 49 | H | H | C$_2$H$_5$ | 0 | CH$_2$CH=CHCH$_2$CH=CHCH$_2$ | |
| 50 | H | H | C$_2$H$_5$ | 0 | (CH$_2$)$_2$CH=CHCH$_2$CH=CH(CH$_2$)$_2$ | |
| 51 | H | H | C$_2$H$_5$ | 0 | (CH$_2$)$_3$CH=CHCH$_2$CH=CH(CH$_2$)$_3$ | |
| 52 | H | H | C$_2$H$_5$ | 0 | (CH$_2$)$_4$CH=CHCH$_2$CH=CH(CH$_2$)$_4$ | |
| 53 | H | H | C$_2$H$_5$ | 0 | (CH$_2$)$_5$CH=CHCH$_2$CH=CH(CH$_2$)$_7$ | |
| 54 | 4-F | 4-F | C$_2$H$_5$ | 0 | (CH$_2$)$_5$CH=CHCH$_2$CH=CH(CH$_2$)$_7$ | |
| 55 | H | H | C$_2$H$_5$ | 0 | (CH$_2$)$_6$CH=CHCH$_2$CH=CH(CH$_2$)$_6$ | |
| 56 | H | H | C$_2$H$_5$ | 0 | (CH$_2$)$_7$CH=CHCH$_2$CH=CH(CH$_2$)$_5$ | |

EXAMPLE 57

8-(4,5-Diphenyl-1H-imidazol-2-ylthio)octanoic acid

To a solution of 5.0 g (0.012 mole) 8-(4,5-diphenyl-1H-imidazol-2-ylthio)octanoic acid ethyl ester in 125 ml ethanol was added, dropwise, a solution of 5.0 g sodium hydroxide in 125 ml water. The reaction mixture was stirred at reflux under nitrogen for 4 hours. The solvent was concentrated to half the volume and the remaining solution was extracted with diethyl ether. This organic layer was discarded. The aqueous layer was acidified to pH=1.0 using 1N hydrochloric acid and then extracted with diethyl ether. The organic layer was dried over magnesium sulfate and the solvent removed under vacuum. The resulting solid was crystallized from ethanol and triturated with hexane to give 2.13 g (0.005 mole) of the title compound as a white solid, mp=160°-162° C. $^1$H NMR(DMSO-d6): δ12.7(s,1H), 12.0(s,1H), 7.6-7.1(m,10H), 3.1(t,2H,J=7Hz), 2.3(t,2H,J=7Hz), 1.8-1.2(m,10H).

EXAMPLE 58

11-(4,5-Diphenyl-1H-imidazol-2-ylthio)undecanoic acid

To a solution of 6.0 g (0.013 mole) 11-(4,5-diphenyl-1H-imidazole-2-ylthio)undecanoic acid ethyl ester in 150 ml ethanol was added, dropwise, a solution of 6.0 g sodium hydroxide in 150 ml water. The reaction mixture was stirred at reflux under nitrogen for 3 hours. The solvent was concentrated to half the volume and the remaining solution was extracted with diethyl ether. This organic layer was discarded. The aqueous layer was acidified to pH=1.0 using 1N hydrochloric acid and then extracted with diethyl ether. The organic layer was dried over magnesium sulfate and the solvent removed under vacuum. The resulting solid was recrystallized from methanol and triturated with diethyl ether to give 4.10 g (0.009 mole) of the title compound as a white solid, mp=193°-195° C. $^1$HNMR(DMSO-d6): δ12.6(s,1H), 7.6-7.1(m,10H), 3.6(t,2H,J=7Hz), 2.3(t,2H,J=7Hz), 1.8-1.1(m,17H).

TABLE 2

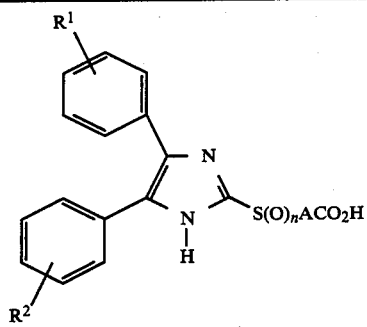

| No | R¹ | R² | n | A | mp (°C.) |
|---|---|---|---|---|---|
| 57 | H | H | 0 | $(CH_2)_7$ | 160-162 |
| 58 | H | H | 0 | $(CH_2)_{10}$ | 193-195 |
| 59 | H | H | 2 | $(CH_2)_7$ | |
| 60 | H | H | 1 | $(CH_2)_7$ | |
| 61 | 4-F | H | 0 | $(CH_2)_7$ | |
| 62 | 4-Cl | H | 0 | $(CH_2)_7$ | |
| 63 | 4-CF₃ | H | 0 | $(CH_2)_7$ | |
| 64 | 4-CH₃ | H | 0 | $(CH_2)_7$ | |
| 65 | 4-F | 4-Cl | 0 | $(CH_2)_7$ | |
| 66 | 4-C₃H₇ | H | 0 | $(CH_2)_7$ | |
| 67 | 4-C₄H₉ | H | 0 | $(CH_2)_7$ | |
| 68 | 4-F | 4-F | 0 | $(CH_2)_7$ | |
| 69 | 4-Cl | 4-Cl | 0 | $(CH_2)_7$ | |
| 70 | 4-CF₃ | 4-CF₃ | 0 | $(CH_2)_7$ | |
| 71 | 4-CH₃ | 4-CH₃ | 0 | $(CH_2)_7$ | |
| 72 | 4-C₂H₅ | 4-C₂H₅ | 0 | $(CH_2)_7$ | |
| 73 | 4-C₃H₇ | 4-C₃H₇ | 0 | $(CH_2)_7$ | |
| 74 | 4-C₄H₉ | 4-C₄H₉ | 0 | $(CH_2)_7$ | |
| 75 | 4-OCH₃ | H | 0 | $(CH_2)_7$ | |
| 76 | 4-OC₂H₅ | H | 0 | $(CH_2)_7$ | |
| 77 | 4-OC₃H₇ | H | 0 | $(CH_2)_7$ | |
| 78 | 4-OC₄H₉ | H | 0 | $(CH_2)_7$ | |
| 79 | 4-OCH₃ | 4-OCH₃ | 0 | $(CH_2)_7$ | |
| 80 | 4-OC₂H₅ | 4-OC₂H₅ | 0 | $(CH_2)_7$ | |
| 81 | 4-OC₃H₇ | 4-OC₃H₇ | 0 | $(CH_2)_7$ | |
| 82 | 4-OC₄H₉ | 4-OC₄H₉ | 0 | $(CH_2)_7$ | |
| 83 | H | H | 0 | $(CH_2)_8$ | |
| 84 | H | H | 0 | $(CH_2)_9$ | |
| 85 | H | H | 0 | $(CH_2)_{10}$ | |
| 86 | H | H | 0 | $(CH_2)_{11}$ | |
| 87 | H | H | 0 | $(CH_2)_{12}$ | |
| 88 | H | H | 0 | $(CH_2)_{13}$ | |
| 89 | H | H | 0 | $(CH_2)_{14}$ | |
| 90 | H | H | 0 | $(CH_2)_{15}$ | |
| 91 | H | H | 0 | $(CH_2)_{16}$ | |
| 92 | H | H | 0 | $(CH_2)_{17}$ | |
| 93 | H | H | 0 | $(CH_2)_{18}$ | |
| 94 | H | H | 0 | $(CH_2)_{19}$ | |
| 95 | H | H | 0 | $(CH_2)_{20}$ | |
| 96 | H | H | 0 | $CH=CH(CH_2)_5$ | |
| 97 | H | H | 0 | $CH_2CH=CH(CH_2)_4$ | |
| 98 | H | H | 0 | $(CH_2)_2CH=CH(CH_2)_3$ | |
| 99 | H | H | 0 | $(CH_2)_3CH=CH(CH_2)_2$ | |
| 100 | H | H | 0 | $(CH_2)_4CH=CHCH_2$ | |
| 101 | H | H | 0 | $(CH_2)_5CH=CH$ | |
| 102 | H | H | 0 | $(CH_2)_8CH=CH(CH_2)_7$ | |
| 103 | H | H | 0 | $CH_2CH=CHCH_2CH=CHCH_2$ | |
| 104 | H | H | 0 | $(CH_2)_2CH=CHCH_2CH=CH(CH_2)_2$ | |
| 105 | H | H | 0 | $(CH_2)_3CH=CHCH_2CH=CH(CH_2)_3$ | |
| 106 | H | H | 0 | $(CH_2)_4CH=CHCH_2CH=CH(CH_2)_4$ | |
| 107 | H | H | 0 | $(CH_2)_5CH=CHCH_2CH=CH(CH_2)_7$ | |
| 108 | 4-F | 4-F | 0 | $(CH_2)_5CH=CHCH_2CH=CH(CH_2)_7$ | |
| 109 | H | H | 0 | $(CH_2)_6CH=CHCH_2CH=CH(CH_2)_6$ | |
| 110 | H | H | 0 | $(CH_2)_7CH=CHCH_2CH=CH(CH_2)_5$ | |

Utility

The compounds of the present invention are inhibitors of the enzyme acyl-CoA:cholesterol acyl-transferase and are thus effective in inhibiting esterification and transport of cholesterol through the intestine and into the lymph.

A. Assay of the Inhibition of Acyl CoA:Cholesterol Acyltransferase (ACAT) in Hepatic Microsomes.

The ability of the compounds of this invention to inhibit ACAT, the enzyme responsible for the intracellular synthesis of cholesteryl esters, was tested as follows. Male Sprague Dawley rats weighing 150-300 g were fed rat chow ad libitum. The animals were fasted for twenty-four hours prior to being sacrificed by decapitation. The livers were perfused in situ with 50 ml of cold 0.25 M sucrose, excised, and homogenized in three volumes of 0.1 M phosphate buffer, pH 7.4 containing 0.5 mM EDTA (ethylenediaminetetraacetic acid), 1.0 mM glutathione, 0.25 M sucrose and 20 μM leupeptin. Microsomes were obtained by differential centrifugation; the supernatant from an initial spin at 15,000×g. for 15 minutes (which removed cell debris and mitochondria) was centrifuged at 105,000×g. for 1 hr to pellet the microsomes. The microsomes were suspended in homogenization buffer reisolated by centrifugation and stored at −70° C. Microsomes were used within one month of preparation.

The control assay in a final volume of 200 μl consisted of 200 μg of microsomal protein, 75 μM $^{14}$C-oleoyl-CoA (10,000 dpm/nmol) in 0.1 M phosphate, pH 7.4 containing 1 mM glutathione. Compounds were added in 5–10 μl of DMSO (dimethyl sulfoxide) and additional controls were run with DMSO only. All components, except the radiolabeled oleoyl-CoA, were preincubated for 15 min at 37° C. prior to the initiation of the reaction by addition of radiolabeled oleoyl-CoA. The assay was terminated after 10 min by the addition of 500 μl of hexane: isopropanol (3:2, v/v). 20,000 dpm of $^{3}$H-cholesteryl oleate and 10 μg of unlabeled cholesteryl oleate and oleic acid were added as an internal standard and carriers, respectively. After allowing 10 min for lipid extraction, the samples were centrifuged at 1,000×g for 10 mins to separate the solvent layers. 200 μl of the top (hexane) layer containing the neutral lipids was spotted onto a Baker SI250-Pa silica gel TLC plate and the plate developed using a hexane: diethyl ether: acetic acid (170:30:1 v/v/v) mobile phase. The lipids were visualized by their interaction with iodine vapor and the cholesteryl ester spot was scraped into a scintillation vial and the radioactivity on the gel was determined by standard liquid scintillation spectrometry. The specific activity of ACAT in control microsomes averaged 260 pmol/min/mg microsomal protein. The % inhibition of the various compounds was the ACAT activity in the presence of the inhibitor divided by the activity of the control (vehicle alone) times 100% − 100.

The ACAT inhibitory activity of the above compounds is shown in Table 3.

B. Assay of the Inhibition of Cholesterol Esterification in Mammalian Cells

The esterification of cholesterol was determined in the murine macrophage-like cell line J774. J774 cells were placed in 60 mm dishes at a density of 200,000 cells per dish in 3.0 ml of Dulbecco's minimal essential medium (DMEM) containing 10% Fetal bovine serum. Cells were incubated at 37° C. in an atmosphere of 5% $CO_2$ and 93% humidity. After 24 hr, the cells were washed with 2 ml of Hanks buffered saline and the media changed to 1.5 ml of DMEM containing 1% Cabosil ® treated serum (CTS) to up-regulate LDL receptors. At 56 hr, fresh media that contained 1% CTS was added to the cells; in all but control dishes the media contained 200 μg LDL/ml to increase the intracellular concentration of cholesterol and promote esterification. At 72 hr, various inhibitors were added to the cells in DMSO (10 μl/ml maximum). At 74 hr, the cells were pulsed with 0.1 mM $^{14}$C-oleic acid (20,000 dpm/nmol) complexed with bovine serum albumin (BSA) to follow cholesteryl ester formation. The experiment was terminated at 76 hrs by washing the monolayers 3 times with 3 ml of Tris-buffered saline at 4° C. The lipids were extracted by incubating the monolayers with 1.5 ml of hexane: isopropanol (3:2, v/v) for 30 mins under gentle agitation. During this period, 20,000 dpm $^{3}$H-cholesteryl linoleate and 10 μg of cholesteryl oleate were added as an internal standard and carrier respectively. The organic solvent was removed and the cells were washed with an additional 1.0 ml of hexane: isopropanol which was combined with the original extract. The cells were allowed to dry overnight, digested with 1.5 ml of 0.2 N sodium hydroxide for 1 hr, and an aliquot of the solubilized protein used for protein determination using the Lowry method. The organic extract was taken to dryness and the residue resuspended in 100 μl of chloroform and the lipids separated on silica gel impregnated glass fiber plates using a hexane: diethyl ether: acetic acid (170:30:1, v/v/v) solvent system. The cholesteryl ester spot was visualized with iodine, cut out, and transferred to scintillation vials to determine the amount of radioactivity. The conversion of oleic acid to cholesteryl ester in the control averaged 0.54 nmol/hr/mg protein and was increased upon the addition of LDL to about 2.37 nmol/hr/mg protein. Inhibition of esterification by various compound was determined by dividing the specific activity (+LDL) in the presence of the inhibitor by the specific activity (+LDL) of the vehicle alone times 100% −100.

The inhibition of esterification by the above compounds is shown in Table 3.

TABLE 3

| | Inhibition of In Vitro Hepatic ACAT Activity and Cholesterol Esterification in Macrophage-Like Cell Line J-774 by Various Compounds | |
|---|---|---|
| Example | IC50 In Vitro ACAT | IC50 Cholesterol Esterification |
| Octimibate* | 23 μM | 78 μM |
| 1 | 2 μM | 19 μM |
| 57 | 2 μM | 80 μM |
| 2 | 1 μM | 17 μM |
| 58 | 1 μM | 17 μM |

*Octimibate is described in U.S. Pat. No. 4,460,598 and has the formula

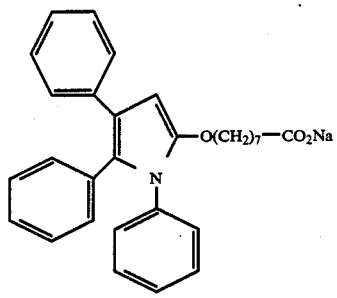

Dosage Forms:

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier.

In the therapeutic use of intestinal ACAT inhibitors, the compounds utilized are administered to the patient at dosage levels of 200 to 2000 mg per day. For a normal male adult human of approximately 70 kg of body weight, this translates into a dosage of 3 to 30 mg per kilogram body weight per day. The dosage administered will, of course, vary depending upon known factors such as the age, health, and weight of the recipient; nature and extent of symptoms, kind of concurrent treatment, frequency of treatment, and the effect desired. Useful pharmaceutical dosage forms for administration of the compounds of this invention can be illustrated as follows:

Tablets

Tablets are prepared by conventional procedures so that the dosage unit is 500 milligrams of active ingredient, 150 milligrams of lactose, 50 milligrams of cellulose and 10 milligrams of magnesium stearate.

Capsules

Capsules are prepared by conventional procedures so that the dosage unit is 500 milligrams of active ingredient, 100 milligrams of cellulose and 10 milligrams of magnesium stearate.

Syrup

| | Wt. % |
|---|---|
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

Aqueous Suspension

| | Wt. % |
|---|---|
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

Resuspendible Powder

| | Wt. % |
|---|---|
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Semi-Solid Gel

| | Wt. % |
|---|---|
| Active Ingredient | 10 |
| Sodium Saccharin | 0.02 |
| Gelatin | 2 |
| Colorant, Flavor and Preservative | as required |
| Water | as required |

Gelatin is prepared in hot water. The finely pulverized active ingredient is suspended in he gelatin solution and then the rest of the ingredients are mixed in. The suspension is filled into a suitable packaging container and cooled down to form the gel.

Semi-Solid Paste

| | Wt. % |
|---|---|
| Active Ingredient | 10 |
| Gelcarin ® (Carrageenin gum) | 1 |
| Sodium Saccharin | 0.01 |
| Colorant, Flavor and Preservative | as required |
| Water | as required |

Gelcarin ® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

Emulsifiable Paste

| | Wt. % |
|---|---|
| Active Ingredient | 30 |
| Tween 80 and Span 80 | 6 |
| Keltrol ® | 0.5 |
| Mineral Oil | 63.5 |

All the ingredients are carefully mixed together to make a homogenous paste.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

What is claimed is:

1. A compound of the formula:

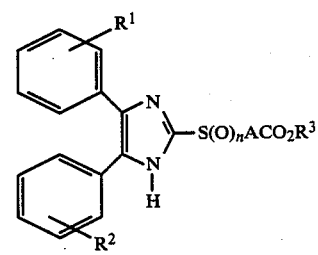

or a pharmaceutically acceptable salt thereof, wherein $R^1$ and $R^2$ independently are H, F, Cl, $CF_3$, alkyl of 1 to 4 carbon atoms, or alkoxy of 1 to 4 carbon atoms;

A is alkylene of 7–20 carbon atoms or an alkenyl residue thereof with no more than 2 double bonds;

$R^3$ is H, $CH_3$ or $C_2H_5$; and n is 0, 1 or 2.

2. A compound of claim 1 wherein $R^1$ and $R^2$ are H.

3. A compound of claim 1 wherein A is alkylene of 7–10 carbon atoms.

4. A compound of claim 1 wherein $R^1$ and $R^2$ are H, and A is alkylene of 7–10 carbon atoms.

5. The compound of claim 1 which is 8-(4,5-diphenyl-1H-imidazol-2-ylthio)octanoic acid ethyl ester.

6. The compound of claim 1 which is 8-(4,5-diphenyl-1H-imidazol-2-ylthio)octanoic acid.

7. The compound of claim 1 which is 11-(4,5-diphenyl-1H-imidazol-2-ylthio)undecanoic acid ethyl ester.

8. The compound of claim 1 which is 11-(4,5-diphenyl-1H-imidazol-2-ylthio)undecanoic acid.

9. A pharmaceutical composition consisting essentially of a pharmaceutically acceptable carrier and an ACAT-inhibitory effective amount of a compound of claim 1.

10. A pharmaceutical composition consisting essentially of a pharmaceutically acceptable carrier and an ACAT-inhibitory amount of a compound of claim 2.

11. A pharmaceutical composition consisting essentially of a pharmaceutically acceptable carrier and an ACAT-inhibitory effective amount of a compound of claim 3.

12. A pharmaceutical composition consisting essentially of a pharmaceutically acceptable carrier and an ACAT-inhibitory effective amount of a compound of claim 4.

13. A pharmaceutical composition consisting essentially of a pharmaceutically acceptable carrier and an ACAT-inhibitory effective amount of the compound of claim 5.

14. A pharmaceutical composition consisting essentially of a pharmaceutically acceptable carrier and an ACAT-inhibitory effective amount of the compound of claim 6.

15. A pharmaceutical composition consisting essentially of a pharmaceutically acceptable carrier and an ACAT-inhibitory effective amount of the compound of claim 7.

16. A pharmaceutical composition consisting essentially of a pharmaceutically acceptable carrier and an ACAT-inhibitory effective amount of the compound of claim 8.

17. A method of inhibiting intestinal absorption of cholesterol in a mammal comprising administering to the mammal an ACAT-inhibitory effective amount of a compound of claim 1.

18. A method of inhibiting intestinal absorption of cholesterol in a mammal comprising administering to the mammal an ACAT-inhibitory effective amount of a compound of claim 2.

19. A method of inhibiting intestinal absorption of cholesterol in a mammal comprising administering to the mammal an ACAT-inhibitory effective amount of a compound of claim 3.

20. A method of inhibiting intestinal absorption of cholesterol in a mammal comprising administering to the mammal an ACAT-inhibitory effective amount of a compound of claim 4.

21. A method of inhibiting intestinal absorption of cholesterol in a mammal comprising administering to the mammal an ACAT-inhibitory effective amount of the compound of claim 5.

22. A method of inhibiting intestinal absorption of cholesterol in a mammal comprising administering to the mammal an ACAT-inhibitory effective amount of the compound of claim 6.

23. The method of inhibiting intestinal absorption of cholesterol in a mammal comprising administering to the mammal an ACAT-inhibitory effective amount of the compound of claim 7.

24. A method of inhibiting intestinal absorption of cholesterol in a mammal comprising administering to the mammal an ACAT-inhibitory effective amount of the compound of claim 8.

* * * * *